United States Patent
Motter et al.

(10) Patent No.: US 8,711,350 B2
(45) Date of Patent: Apr. 29, 2014

(54) TEST METHOD FOR INSPECTION DEVICE, PARTICULARLY FOR LABEL SEATING INSPECTION DEVICE

(75) Inventors: Theo Motter, Stolberg (DE); Frank Fischer, Pfaffen-Schwabenheim (DE)

(73) Assignee: KHS GmbH, Dortmund (DE)

( * ) Notice: Subject to any disclaimer, the term of this patent is extended or adjusted under 35 U.S.C. 154(b) by 373 days.

(21) Appl. No.: 13/063,250

(22) PCT Filed: Oct. 7, 2009

(86) PCT No.: PCT/EP2009/007190
§ 371 (c)(1),
(2), (4) Date: Mar. 10, 2011

(87) PCT Pub. No.: WO2010/040512
PCT Pub. Date: Apr. 15, 2010

(65) Prior Publication Data
US 2011/0164257 A1   Jul. 7, 2011

(30) Foreign Application Priority Data
Oct. 7, 2008   (DE) .................. 10 2008 050 249

(51) Int. Cl.
*G01N 21/00* (2006.01)
*G01N 21/90* (2006.01)
*B07C 5/12* (2006.01)
*B07C 5/34* (2006.01)
*H04N 5/253* (2006.01)
*H04N 7/18* (2006.01)

(52) U.S. Cl.
USPC ............... 356/240.1; 356/239.1; 250/223 B; 348/92; 348/127; 382/142

(58) Field of Classification Search
None
See application file for complete search history.

(56) References Cited

U.S. PATENT DOCUMENTS

| | | | | |
|---|---|---|---|---|
| 4,413,738 A | * | 11/1983 | Pemberton et al. | 209/523 |
| 4,691,231 A | * | 9/1987 | Fitzmorris et al. | 348/127 |
| 4,996,658 A | * | 2/1991 | Baker | 702/97 |
| 5,546,819 A | | 8/1996 | Zodrow | |
| 5,755,335 A | * | 5/1998 | Michelotti et al. | 209/528 |
| 6,072,575 A | * | 6/2000 | Loll | 356/239.4 |
| 6,448,549 B1 | * | 9/2002 | Safaee-Rad | 250/223 B |
| 6,466,691 B1 | * | 10/2002 | Heuft | 382/142 |
| 6,597,804 B1 | * | 7/2003 | Heuft | 382/142 |
| 6,912,303 B2 | * | 6/2005 | Heuft | 382/142 |
| 7,265,662 B2 | * | 9/2007 | Belanger | 340/521 |
| 7,509,786 B2 | | 3/2009 | Thatenhorst | |
| 7,832,181 B2 | * | 11/2010 | Schroeder et al. | 53/53 |
| 8,064,049 B2 | * | 11/2011 | Widera | 356/239.4 |
| 2003/0012421 A1 | * | 1/2003 | Werzinger | 382/142 |
| 2005/0121104 A1 | * | 6/2005 | Monzel | 141/144 |
| 2005/0263443 A1 | | 12/2005 | Martin et al. | |
| 2006/0081512 A1 | * | 4/2006 | Daniel | 209/599 |
| 2007/0017593 A1 | | 1/2007 | Bernhard | |
| 2010/0257919 A1 | * | 10/2010 | Matsushita et al. | 73/49.3 |
| 2011/0102782 A1 | * | 5/2011 | Wiemer et al. | 356/239.4 |
| 2012/0059615 A1 | * | 3/2012 | Pschichholz | 702/82 |
| 2013/0271755 A1 | * | 10/2013 | Lindner | 356/240.1 |

FOREIGN PATENT DOCUMENTS

| | | |
|---|---|---|
| DE | 3314730 | 10/1984 |
| DE | 3324449 | 1/1985 |
| DE | 4200798 | 7/1993 |
| DE | 4302656 | 5/1994 |
| DE | 4441245 | 5/1996 |
| DE | 102004005994 | 9/2005 |
| EP | 0287018 | 10/1988 |
| EP | 0613732 | 9/1994 |
| EP | 1593971 | 11/2005 |
| EP | 1627816 | 2/2006 |
| EP | 1628241 | 2/2006 |
| JP | 2008-128944 | 6/2008 |
| WO | 2006/011803 | 2/2006 |
| WO | WO 2007131673 A1 * | 11/2007 |

* cited by examiner

*Primary Examiner* — Gordon J Stock, Jr.
(74) *Attorney, Agent, or Firm* — Occhiuti & Rohlicek LLP

(57) ABSTRACT

The invention relates to a test method for checking an inspection device, comprising at least the steps of: generating a prescribed number of faulty and/or correctly labelled containers or test containers; moving the faulty containers or test containers past the inspection device, which detects the faulty containers or test containers and generates a signal for ejecting the faulty containers or test containers, or indicates a value relative to the expected and the measured faulty and/or correctly labelled containers. The test method can be started or performed manually or automatically, and is suitable, for example, for checking a label seating inspection device for correct functionality, or optionally for confirming the faulty functioning thereof.

20 Claims, No Drawings

TEST METHOD FOR INSPECTION DEVICE, PARTICULARLY FOR LABEL SEATING INSPECTION DEVICE

CROSS-REFERENCE TO RELATED APPLICATIONS

This application is the National Stage of International Application No. PCT/EP2009/007190, filed on Oct. 7, 2009, which claims the priority of German Patent Application No. 10 2008 050 249.9, filed on Oct. 7, 2008. The contents of both applications are hereby incorporated by reference in their entirety.

The invention concerns a test method for checking an inspection device.

DE 10 2004 005 994 A1 discloses a labelling machine. This has a device for feeding labels and a labelling unit. The labelling unit has a label holder, a glue roller, a rotatable carrier provided with gluable removal segments, and a gripping cylinder. So, for example, bottles can be provided with labels, whereby the labelling machine can be designed e.g. as a rotary, a linear or again, as a horizontal labelling machine. A label seating inspection device is located in the outlet area of the labelled bottles, with which the desired arrangement of labels on the bottles is monitored. It is possible to check the labels for correct seating, for example with respect to design features arranged on the bottles (known as embossings). It is also possible to check neck and shoulder labels for correct alignment with respect to each other or also with respect to the design features. If there is any variation in the seating of the label outside a prescribed tolerance, the label seating inspection device sends corresponding signals to trigger a correction device, which acts on the labelling units, so that a correct label seating can be achieved. Naturally, any bottles not provided with a correctly aligned label are sorted out in an ejection device, which is obviously also possible via the corresponding generated signal from the label seating inspection device.

DE 44 41 245 A1 discloses a method for controlling labelled containers. The control device is integrated into a labelling machine, and has a laser distance meter. The laser distance meter can be used to determine whether or not a container is provided with a label. During an active measurement interval, the laser beam emitted from the laser distance meter firstly strikes the surface of a bottle moving past and measures its distance from its fixed housing, which thus forms the constant reference location. As soon as the laser beam strikes the surface of the label, there arises an abrupt reduction of the instantaneously measured distance corresponding to the thickness of the label and, if there is one, of the glue film between the bottle and the label. This abrupt change in distance is captured in an evaluation unit and assessed as a criterion for the presence of a label. Accordingly, the evaluation unit sends no signal or a Good signal to a sorting device. If there is no label on the bottle, nor is an abrupt change in distance detectable, so that the evaluation unit emits an error signal to the sorting device, which sorts out the corresponding bottle. The main disadvantage to be seen therein is that the control device can only determine whether there is a label on the bottle or not. However, it is not possible to determine whether the label is also correctly aligned, for example with respect to design features, or has creases.

By way of example, bottles or similar containers are filled by means of a filling device with a bulk product, in order then to be fed to a labelling machine. The containers are aligned in the labelling machine or beforehand, for example in relation to design features (known as embossings), so that the labels can be applied to the containers in alignment with the design features. The labelled containers are aligned again, and led or conveyed past an inspection device, which can be in the form of a label seating inspection device. If the label seating inspection device detects containers with a bad or faulty label seating, a signal is generated for ejection. The ejected containers, for example bottles, are stored on a separate conveyor.

Obviously, the inspection device, for example when designed as a label seating inspection device, requires a test for correct function. This can, for example, be done by checking the ejected containers. This procedure is, however, very time-consuming and unreliable, as in particular containers which have not been ejected can only be randomly inspected, as the container flow moves at high speed. Labelling machines for example have a throughput of up to 60,000 containers or bottles per hour.

The invention is therefore based on the problem of specifying a test method for checking an inspection device, particularly a label seating inspection device, with which the aforementioned disadvantages are avoided.

The problem is solved according to the invention by a test method with the features of claim 1, comprising at least the steps of: generating a prescribed number of containers, known as test containers; leading the test containers past the inspection device, which detects the test containers and ideally generates a control signal.

Using the invention, inspection devices can reliably be checked for correct function. Advantageously, for this purpose an individually prescribed number of test containers is generated, which are led past the inspection device. The inspection device should, if it is functioning correctly, also send a corresponding signal for ejecting at least faulty containers to a sorting device. Naturally, an evaluation unit can be connected between them. If the inspection device detects all faulty containers, or if all faulty test containers have been ejected, and leaves fault-free test containers in the container flow, it is guaranteed that the inspection device is functioning correctly.

In one advantageous embodiment, provision is made that the prescribed number of test containers with faulty and/or correct label seating are introduced in a conveyor path upstream of the inspection device, the inspection device taking the form of a label seating inspection device, and the containers being led past this, and the label seating inspection device inspects the test containers and generates a measured value, by means of which the number of test containers with faulty and/or correct label seating can be determined, whereby, using the measured value, the deviation between the target measured value and the actual measured value can be determined, whereby ideally the target measured value is the prescribed number of test containers, with faulty and/or correct label seating and the actual measured value is the number of test containers with faulty and/or correct label seating measured or detected by the inspection device.

Advantageously in the sense of the invention, provision can be made that when the inspection device generates a signal for ejecting at least the test containers with faulty or correct label seating and ideally for test containers with both types of label seating.

Advantageously in the sense of the invention, at least one test container may have a special test marking, in the form of a test embossing, a test label, a test overprint or similar, whereby the test marking is taught to a capture unit, for example the alignment station of a labelling machine, and the test feature defines at least the start of a test program.

Advantageously, provision can be made that the at least one test container is introduced into the transport path upstream of a labelling machine, said test container being detected as such by appropriate inspection or measurement systems, and according to the inspection or measurement systems, the subsequent labelling device or treatment station of a labelling device is controlled in such a way that the labelling function, in relation to the at least one test bottle or in relation to the at least one test container, is switched off.

In one advantageous embodiment the inspection device is assigned to a labelling machine, whereby the inspection device in a preferred embodiment is designed as a label seating inspection device of prior art. In the labelling machine, containers of all kinds, for example bottles, can be provided with different labels, which each indicate different bulk products. The labelling machine can for example have an identifier station for design features (known as embossings) and an alignment station, whereby both stations can naturally also be integrated into a common station.

Advantageously, provision can be made that firstly a label of a certain sort is taught to the alignment station, so that an alignment feature is defined as test program. In this case, it is advantageous if the label to be taught in is aligned correctly with the potential embossings and applied correctly to the container. In advantageous fashion, the test function in the alignment station is switched off after being taught the new sort of label, at least with respect to the recognition of embossings.

With the label sort thus taught, the individually prescribed number of faulty containers is generated. This means that containers, for example bottles, are incorrectly provided with labels of the taught sort. For example, the labels may be arranged at an angle with respect to the potential embossing, or for example have creases. The generation of the individually prescribed number of faulty containers can for example be done manually. Obviously in each test method or test program, a different number of faulty containers can be generated, which is what is meant by the term of individually prescribing the number in the sense of the invention.

The faulty test containers are introduced into the labelling machine, or suspended or set in the transport path of the bottles and moved past the alignment station into the labelling machine. Naturally, the labelling machine is switched off during the test process and/or during the test program, at least with respect to its labelling function.

The faulty test containers should, if the inspection device or label seating inspection device are functioning correctly, be recognised by this, so that a signal for ejecting the faulty containers is generated in known fashion.

For further checking of the inspection device or label seating inspection device, provision can also naturally be made to lead at least one container provided with a correctly applied label past the inspection device, which should then, if the inspection device or label seating inspection device is functioning correctly, not be ejected or preferably is ejected but is marked as being correct. In a preferred embodiment of the method, provision can be made to generate a complete flow of test containers, which is formed by an individually prescribed number of faulty and correct test containers, so that a complete flow of test containers consisting of correctly labelled and incorrectly labelled test containers is generated. This complete flow of test containers is moved into the labelling machine and led past the inspection device or label seating inspection device. If the inspection device or label seating inspection device is functioning correctly, the respective correct test containers will thereby remain in the test container flow, while the faulty test containers are ejected. Naturally, here, too, the correct test containers can be ejected, but then again, marked as correct.

The invention provides a test method for checking an inspection device or in the preferred embodiment as label seating inspection device with which this can be checked for correct function regularly, for example daily, before each shift change and/or before a change of type. The inspection device and/or the label seating inspection device can thereby, in a preferred embodiment, be connected to an inspection screen, so that immediately after the containers pass by the inspection device and/or the label seating inspection device, the result is visible, while at the same time an instantaneous statement can be made about a correct function of the inspection device and/or of the label seating inspection device. In one advantageous embodiment, provision can be made that at least the number of faulty containers is stored in the inspection device. Naturally, the number of containers in the complete flow of test containers, divided into "Good" and/or "Bad containers" can also be stored in the inspection device.

Once the test method and/or the previously described test program has been completed, the labelling machine mentioned by way of example can be reset to its original function, which means that e.g. the alignment station and the labelling function can again be switched on manually.

In the test method described so far, manual procedures have been followed, which means that the functions of the exemplary labelling machine have been switched off manually. In a refinement of the test method according to the invention, provision can be made to carry this out automatically.

In that case, provision is made, as above, for the exemplary labelling machine firstly that preferably a correct container is taught to the alignment station, so that an alignment feature is defined as test program.

According to the invention, the problem is also solved by a test method with the features of claim 11, comprising at least the steps of: generating a prescribed number of incorrectly labelled test containers; leading the incorrectly labelled test containers past the inspection device, which detects those which are incorrectly labelled and ideally generates a signal for ejecting the incorrectly labelled test containers, while in the test method at least the following steps: generation of incorrectly and correctly labelled test containers; leading the test containers past the inspection device, which detects the at least incorrectly or correctly labelled test containers and ideally generates at least one signal for ejecting the incorrectly or correctly labelled test containers, are carried out.

For the method to be carried out automatically, advantageously at least one test container can be generated which is introduced into the container flow with a unique, particular feature, thus for example with a unique sticker and/or a unique design feature (embossing). Preferably, again, an individually prescribed number of test containers or test bottles is manually generated. These test containers are provided, in the preferred embodiment, with incorrectly (manually) applied labels of the taught sort. The test containers are introduced into the container flow and guided to the exemplary labelling machine. Advantageously, the alignment station thereby recognises the test containers by the unique feature and generates a signal to the exemplary labelling machine or to the inspection device in the exemplary embodiment as label seating inspection device, so that a test program can be detected. The test containers are moved into the exemplary labelling machine, which, as a result of the generated signal of running the test method and/or the test program, automatically switches off its labelling function. Also, the function of the alignment station is turned off, at least with respect to its embossing recognition.

The faulty test containers should, if the inspection device or label seating inspection device are functioning correctly, be recognised by this, so that in known fashion a signal for ejecting the faulty test containers is generated.

For further checking of the inspection device or the label seating inspection device, provision can naturally also be made to lead at least one test container with a correctly applied label past the inspection device, which then, if the inspection device or label seating inspection device are functioning correctly, should not be ejected, or preferably is ejected but is marked as correct.

In a preferred embodiment of the method, provision can be made to generate a complete flow of test containers which is composed of a prescribed number of faulty and correct test containers, i.e. that a complete flow of test containers consisting of correctly labelled and incorrectly labelled containers is generated. This complete flow of test containers is fed into the labelling machine and led past the inspection device or label seating inspection device. If the inspection device or label seating inspection device are functioning correctly, the respective correct test containers will thereby remain in the test container flow, while the faulty test containers are ejected. Naturally, here, too, the correct test containers can be ejected, but then again, marked as correct.

Also, with this embodiment a test method for checking an inspection device or in the preferred embodiment as label seating inspection device is provided with which this can be checked for correct function regularly, for example daily, before each shift change and/or before a change of type. The inspection device or label seating inspection device can thereby, in a preferred embodiment, be connected to an inspection screen, so that immediately after the containers pass by the inspection device or label seating inspection device, the result is visible, while at the same time a statement can be made about a correct function of the inspection device or label seating inspection device. In one advantageous embodiment, provision can be made that at least the number of faulty containers is stored in the inspection device. Naturally, the number of test containers in the complete flow of test containers, divided into "Good" and/or "Bad containers" can also be stored in the inspection device.

Following completion of the test method and/or of the previously described test program, said exemplary labelling machine is reset to its original function, which means that e.g. the alignment station and the labelling function are turned on again. This, too, can advantageously take place automatically, when the inspection device or label seating inspection device, when comparing the stored number of test containers (faulty and/or total test containers), detects that all test containers have run through, and the test method is complete.

In a further embodiment of the test method, provision can be made that the test containers are automatically led into the container flow of, for example, containers or bottles to be labelled via a lock and/or storage system regularly and/or in special situations (e.g. daily, shift change, type change) and are led out of these again in order to check the inspection device or label seating inspection device for correct function. In this case, the test containers can be collected sorted and for example stored in a collecting box, which an operator brings to the inlet point of the exemplary labelling machine. Naturally the collecting box can also be brought mechanically to the inlet point. It is naturally also possible for the test containers collected in the storage system to be transported automatically to the inlet point.

The invention is suitable in preferred application for labelling machines and/or for their label seating inspection device. In this respect, the test method according to the invention can be carried out on labelling machines for checking the In-labeler label seating- and embossing alignment check, so that an operator of the labelling machine can carry out a check at any time, of whether this is functioning correctly, or whether for example servicing works and/or adjustment actions are necessary. Obviously, however, it is also possible to check other inspection devices for correct function by means of a prescribed number of Bad containers (and Good containers). For example, it is possible to check a fill level inspection device with a corresponding test method, to name just one example of further application of the test method according to the invention.

The invention claimed is:

1. A method for testing container inspection, said method comprising generating a prescribed number of test containers, leading the test containers past where containers are to be inspected, while the test containers are where containers are to be inspected, detecting the test containers and generating a control signal, generating a complete test container flow having a prescribed number of faulty and correct test containers, leading the complete test container flow past where containers are to be inspected, and, while the containers are where containers are to be inspected, generating a signal for ejecting faulty test containers from the test container flow, whereby correct test containers remain in the test container flow.

2. The method of claim 1, further comprising causing generation of a signal for ejecting test containers with at least one of faulty and correct label seating.

3. The method of claim 1, further comprising providing at least one test container with a special test marking selected from a group consisting of a test embossing, a test label, and a test overprint, teaching the test marking to a capture unit, wherein the test marking defines at least the start of a test program.

4. The method of claim 1, further comprising feeding at least one test container into a transport path upstream of a labeling machine having a labeling function, and when the container is where containers are either inspected or measured, detecting the test container, and, according to data that results from either inspecting or measuring the container, switching off the labeling function of the downstream labeling machine or treatment station in relation to the at least one test container.

5. The method of claim 1, further comprising moving the prescribed number of test containers into a labeling machine, leading the test containers past where seating of labels on containers is to be inspected, and, while the test containers are where seating of labels on containers is to be inspected generating a signal for ejecting each faulty test container.

6. The method of claim 1, wherein leading containers to where containers are to be inspected comprises leading the containers to a portion of a labeling machine at which seating of labels on containers is to be inspected.

7. The method of claim 6, further comprising: feeding a prescribed number of test containers with faulty and/or correct label seating into a transport path upstream of past where containers are to be inspected, and, while the containers are being led past where containers are to be inspected, inspecting the test containers, and generating a measured value, the measured value being indicative of a number of test containers with faulty and/or correct label seating.

8. A method for checking container inspection, said method comprising generating a prescribed number of incorrectly labeled test containers, leading the incorrectly labeled test containers past where containers are to be inspected, and, while the containers are being led past where containers to be inspected, detecting incorrectly labeled test containers and generating a signal for ejecting the incorrectly labeled test containers, introducing, into a container flow, a test container having a unique feature, at an alignment station of a labeling machine, said alignment station having a detection function, recognizing the unique feature and generating a signal representative thereof, detecting, by a test program, said signal, and, in response to detection of said signal, turning off the detection function of the alignment station, and turning off a labeling function of said labeling machine.

9. The method of claim 8, further comprising:
including correctly labeled test containers; leading the test containers, which include incorrectly labeled and correctly labeled test containers, past where containers are to be inspected, and, while there, detecting and distinguishing between incorrectly and correctly labeled test containers and generating at least one signal for taking action on the basis of whether a test container is an incorrectly or correctly labeled test container.

10. The method of claim 8, further comprising:
detecting the faulty test containers where inspection is being carried out, and generating a signal for ejecting the faulty test containers.

11. The method of claim 8, further comprising leading at least one test container with a correctly applied label past where the containers are to be inspected.

12. The method of claim 8, further comprising generating a complete test container flow having a prescribed number of faulty and fault-free test containers.

13. The method of claim 8, further comprising leading test containers past where containers are to be inspected regularly via a lock and storage system.

14. The method of claim 8, wherein leading containers past where containers are to be inspected comprises leading containers past where label seating on containers is to be inspected.

15. A method for checking container inspection, said method comprising generating a prescribed number of incorrectly labeled test containers, leading the incorrectly labeled test containers past where containers are to be inspected, while the containers are where containers are to be inspected, detecting incorrectly labeled test containers and generating a signal for ejecting the incorrectly labeled test containers, including correctly labeled test containers, leading the test containers, which include incorrectly labeled and correctly labeled test containers, past where containers are to be inspected, and while the containers are where containers are to be inspected, detecting and distinguishing between incorrectly and correctly labeled test containers and generating at least one signal for taking action on the basis of whether a test container is an incorrectly or correctly labeled test container.

16. The method of claim 15, further comprising, detecting the faulty test containers where the containers are being inspected, and generating a signal for ejecting the faulty test containers.

17. The method of claim 15, further comprising leading at least one test container with a correctly applied label past where containers are being inspected.

18. The method of claim 15, further comprising generating a complete test container flow having a prescribed number of faulty and fault-free test containers.

19. The method of claim 15, further comprising leading test containers past where containers are being inspected regularly via a lock and storage system.

20. The method of claim 15, wherein leading containers past where containers are to be inspected comprises leading containers past where label seating of labels on containers is to be inspected.

\* \* \* \* \*